(12) United States Patent
Kajiura et al.

(10) Patent No.: US 12,117,386 B2
(45) Date of Patent: Oct. 15, 2024

(54) INSPECTION DEVICE AND INSPECTION METHOD FOR PILLAR-SHAPED HONEYCOMB FILTER

(71) Applicant: NGK INSULATORS, LTD., Nagoya (JP)

(72) Inventors: Yohei Kajiura, Nagoya (JP); Yuji Watanabe, Kasugai (JP); Yoshihiro Sato, Nissin (JP); Yuichi Tajima, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 367 days.

(21) Appl. No.: 17/650,400

(22) Filed: Feb. 9, 2022

(65) Prior Publication Data

US 2022/0404261 A1 Dec. 22, 2022

Related U.S. Application Data

(63) Continuation of application No. PCT/JP2021/036519, filed on Oct. 1, 2021.

(30) Foreign Application Priority Data

Jun. 18, 2021 (JP) ................................. 2021-101991

(51) Int. Cl.
*G01N 15/1434* (2024.01)
*G01N 15/06* (2024.01)
(Continued)

(52) U.S. Cl.
CPC . *G01N 15/1434* (2013.01); *G01N 2015/0662* (2013.01); *G01N 2015/084* (2013.01); *G01N 2015/1486* (2013.01); *G01N 33/0004* (2013.01)

(58) Field of Classification Search
None
See application file for complete search history.

(56) References Cited

U.S. PATENT DOCUMENTS

| 4,361,028 A | 11/1982 | Kamiya et al. |
| 2002/0144535 A1* | 10/2002 | Sakata ............... G01N 15/1456 73/1.03 |

(Continued)

FOREIGN PATENT DOCUMENTS

| CN | 101738361 A * | 6/2010 | ......... B01D 46/0086 |
| JP | S56-118641 A | 9/1981 | |

(Continued)

OTHER PUBLICATIONS

International Search Report and Written Opinion (Application No. PCT/JP2021/036519) dated Nov. 9, 2021.

*Primary Examiner* — Rufus L Phillips
(74) *Attorney, Agent, or Firm* — BURR PATENT LAW, PLLC

(57) ABSTRACT

An inspection device for a pillar shaped honeycomb filter includes: a housing portion that can house a pillar shaped honeycomb filter; an introduction pipe and a discharge pipe through which a gas can flow, each of the introduction pipe and the discharge pipe being connected to the housing portion; a particle generation portion for generating particles; a particle introduction portion for introducing the particles generated by the particle generation portion into the introduction pipe; a gas stirring portion arranged in the introduction pipe on an upstream side of the particle introduction portion in a gas flow direction; and particle counters for measuring the number of particles, the particle counters being arranged in the introduction pipe and the discharge pipe on a downstream side of the particle introduction portion in the gas flow direction.

22 Claims, 4 Drawing Sheets

(51) Int. Cl.
*G01N 15/08* (2006.01)
*G01N 15/14* (2024.01)
*G01N 33/00* (2006.01)

(56) References Cited

U.S. PATENT DOCUMENTS

| | | | |
|---|---|---|---|
| 2003/0174306 A1* | 9/2003 | Grant | G01N 35/1097 |
| | | | 356/36 |
| 2011/0048109 A1 | 3/2011 | Suman et al. | |
| 2020/0254435 A1 | 8/2020 | Wu et al. | |
| 2021/0302296 A1 | 9/2021 | Sato et al. | |
| 2022/0326204 A1* | 10/2022 | Yamada | G01N 33/0047 |
| 2023/0123798 A1* | 4/2023 | Sando | G01N 1/38 |
| | | | 73/232 |

FOREIGN PATENT DOCUMENTS

| | | |
|---|---|---|
| JP | S57-167729 A | 10/1982 |
| JP | 2001-305042 A | 10/2001 |
| JP | 2010-223877 A | 10/2010 |
| JP | 2013-029501 A | 2/2013 |
| JP | 6756939 B1 | 9/2020 |

* cited by examiner

INSPECTION DEVICE AND INSPECTION METHOD FOR PILLAR-SHAPED HONEYCOMB FILTER

FIELD OF THE INVENTION

The present invention relates to an inspection device and an inspection method for a pillar shaped honeycomb filter.

BACKGROUND OF THE INVENTION

Particulate matters such as soot (hereinafter referred to as PMs: Particulate Matters) are contained in an exhaust gas discharged from an internal combustion engine such as diesel engines and gasoline engines. The PMs such as soot are harmful to the human body and emission of the PMs is regulated. Currently, filters represented by diesel particulate filters (DPFs) and gasoline particulate filters (GPFs) for passing an exhaust gas through a small porous partition wall to filter the PMs such as soot, are widely used in order to comply with exhaust gas regulations.

Known as a filter for collecting the PMs such as soot is a wall flow type pillar shaped honeycomb structure (hereinafter, also referred to as a "pillar shaped honeycomb filter") including: a partition wall that defines a plurality of first cells and second cells each extending from a first end face to a second end face, wherein the first cells and the second cells are arranged to be adjacent to each other across the partition wall, and the first end face of each first cell and the second end face of each second cell are opened, and the second end face of each first cell and the first end face of each second cell are provided with a plugged portion.

In recent years, with tightening of exhaust gas regulations, stricter PM emission standards (PN regulation: Particle Matter Number Regulation) have been introduced, and higher PM collection performance (PN collection efficiency) is required for filters.

A conventional inspection method is known which feeds soot particles having a median particle size of 300 nm to a filter, measures the number of soot particles before and after being fed to the filter by means of a particle counter, and determines a difference between them (Patent Literature 1). Further, also known is a method of feeding a gas containing fine particles to a first end face of a pillar shaped honeycomb filter, and irradiating a second end face with a sheet-like light parallel to the second end face so as to cover the entire second end face, and imaging the entire second end face with a camera (Patent Literature 2).

PRIOR ART

Patent Literatures

[Patent Literature 1] U.S. Patent Application Publication No. 2020/0254435 A1
[Patent Literature 2] Japanese Patent No. 6,756,939 B

SUMMARY OF THE INVENTION

The present invention relates to an inspection device for a pillar shaped honeycomb filter, wherein the inspection device comprises:
a housing portion that can house a pillar shaped honeycomb filter;
an introduction pipe and a discharge pipe through which a gas can flow, each of the introduction pipe and the discharge pipe being connected to the housing portion;
a particle generation portion for generating particles;
a particle introduction portion for introducing the particles generated by the particle generation portion into the introduction pipe;
a gas stirring portion arranged in the introduction pipe on an upstream side of the particle introduction portion in a gas flow direction; and
particle counters for measuring the number of particles, the particle counters being arranged in the introduction pipe and the discharge pipe on a downstream side of the particle introduction portion in the gas flow direction.

Further, the present invention relates to an inspecting method for a pillar shaped honeycomb filter, wherein the method comprises:
a particle generation step of generating particles;
a particle introduction step of introducing the particles generated in the particle generation step into a gas stirred by a gas stirring portion;
a particle feed step of feeding the gas having the introduced particles to the pillar shaped honeycomb filter; and
a particle measurement step of measuring the number of particles in the gas on an upstream side and a downstream side of the pillar shaped honeycomb filter in a gas flow direction.

DETAILED DESCRIPTION OF THE INVENTION

In the inspection method of Patent Literature 1, an amount of soot particles fed tends to change depending on positions in the filter. This is because, in the inspection method of Patent Literature 1, it difficult to stir the soot particles, so that the concentration distribution of the soot particles is deviated in a plane orthogonal to a feed direction of the soot particles. Therefore, even if the same product is inspected, the measured value may vary depending on the direction of the filter and the arrangement method, so that the inspection accuracy of the collection performance may be deteriorated.

Further, the inspection method of Patent Literature 2 simply evaluates the difference in brightness on the image based on the fact that the sheet-like light is scattered when it hits the fine particles. Therefore, it cannot be said that the inspection accuracy of the collection performance is sufficient.

The present invention has been made to solve the above problems. An object of the present invention is to provide an inspection device and an inspection method for a pillar shaped honeycomb filter, which have higher inspection accuracy of collection performance.

The present inventors have found that the inspection accuracy of the collection performance can be improved by providing a gas stirring portion at a predetermined position of the inspection device for the pillar shaped honeycomb filter to stir effectively the particles and suppress the deviation of the concentration distribution of soot particles in a plane perpendicular to a gas flow direction X, and they have completed the present invention.

According to the present invention, it is possible to provide an inspection device and an inspection method for a pillar shaped honeycomb filter, which have higher inspection accuracy of collection performance.

Hereinafter, embodiments of the present invention will be specifically described with reference to the drawings. It is to understand that the present invention is not limited to the following embodiments, and those which have appropriately added changes, improvements and the like to the following embodiments based on knowledge of a person skilled in the art without departing from the spirit of the present invention fall within the scope of the present invention.

(1) Inspection Device for Pillar Shaped Honeycomb Filter

Figure 1:
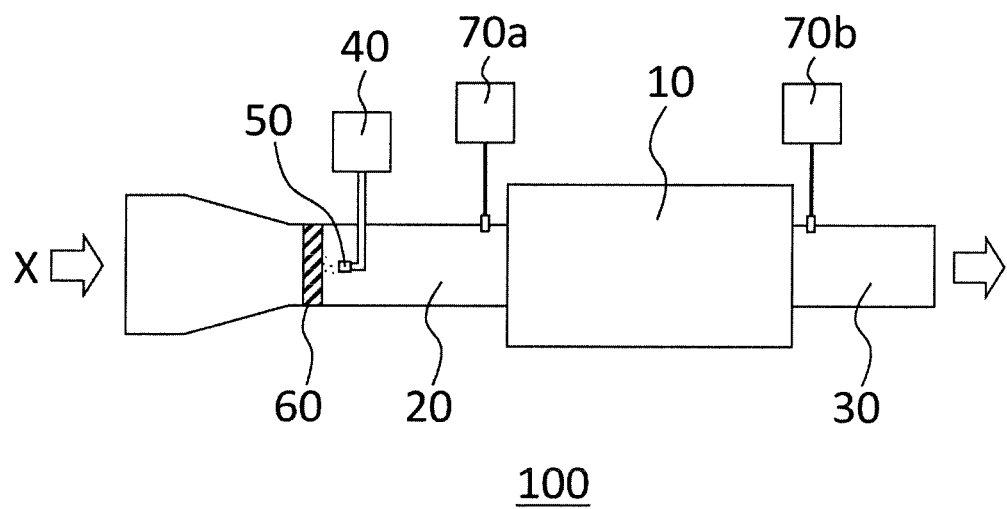
FIG. 1 is a schematic view of an inspection device for a pillar shaped honeycomb filter according to an embodiment of the present invention.

FIG. 1 is a schematic view of an inspection device for a pillar shaped honeycomb filter according to an embodiment of the present invention.

As shown in FIG. 1, an inspection device 100 for a pillar shaped honeycomb filter includes: a housing portion 10 that can house a pillar shaped honeycomb filter; an introduction pipe 20 and a discharge pipe 30 through which a gas can flow, and which are connected to the housing portion 10; a particle generation portion 40 for generating particles; a particle introduction portion 50 for introducing the particles generated by the particle generation portion 40 into the introduction pipe 20; a gas stirring portion 60 arranged in the introduction pipe 20 on an upstream side of the particle introduction portion 50 in a gas flow direction X; and particle counters 70*a*, 70*b* which are respectively arranged in the introduction pipe 20 and the discharge pipe 30 on the downstream side of the particle introduction portion 50 in the gas flow direction X and which measure the number of particles. Such a structure leads to easy diffusion of the particles into the gas, so that any deviation of a concentration distribution of the particles in a plane perpendicular to the gas flow direction X can be suppressed. Then, the number of the particles is measured by the particle counters 70*a*, 70*b* using the particles in which the deviation of the concentration distribution has been suppressed, so that inspection accuracy of collection performance can be improved.

It should be noted that FIG. 1 shows an example in which members such as the introduction pipe 20 and the discharge pipe 30 are horizontally arranged, but these members may be vertically arranged.

Hereinafter, each component of the pillar shaped honeycomb filter to be inspected and the inspection device 100 for the pillar shaped honeycomb filter will be described in detail.

<Pillar Shaped Honeycomb Filter>

The pillar shaped honeycomb filter used in the inspection device 100 for the pillar shaped honeycomb filter is a wall flow type pillar shaped honeycomb structure. The pillar shaped honeycomb filter can be used as DPF and GPF for collecting PMs such as soot, which are attached to an exhaust gas line from a combustion device, typically an engine mounted on a vehicle.

Figure 2:
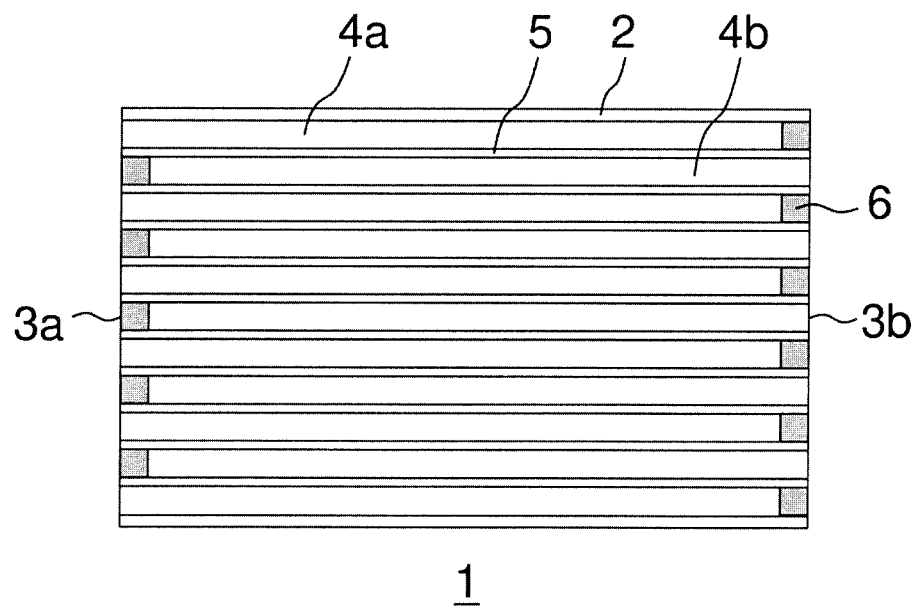
FIG. 2 is a cross-sectional view of a pillar shaped honeycomb filter used for an inspection device for a pillar shaped honeycomb filter according to an embodiment of the present invention.
Figure 3:
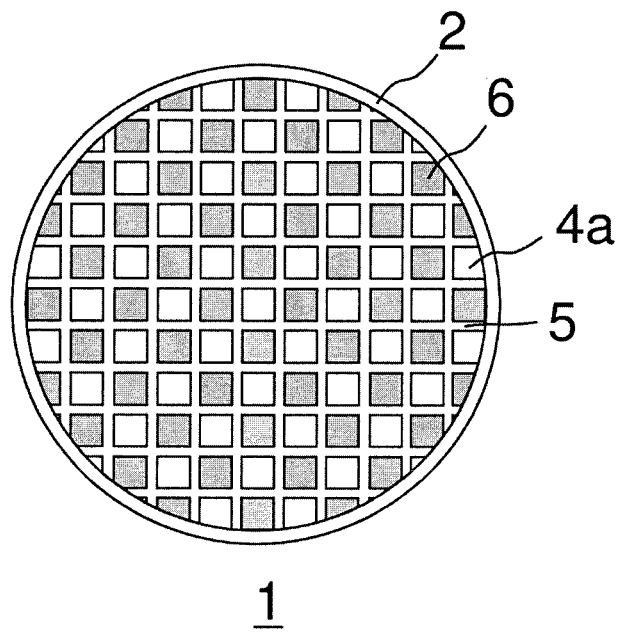
FIG. 3 is an end view of the pillar shaped honeycomb filter in FIG. 2.

FIGS. 2 and 3 are a schematic cross-sectional view (cross-sectional view parallel to an extending direction of cells) and an end view (end view of a first end face) of the pillar shaped honeycomb filter.

As shown in FIGS. 2 and 3, the pillar shaped honeycomb filter 1 includes: an outer peripheral wall 2; a plurality of first cells 4*a* arranged on an inner side of the outer peripheral wall 2, each of the first cells 4*a* extending from a first end face 3*a* to a second end face 3*b*, the first end face 3*a* being opened and the second end face 3*b* having a plugged portion 6; a plurality of second cells 4*b* arranged on the inner side of the outer peripheral wall 2, each of the second cells 4*b* extending from the first end face 3*a* to the second end face 3*b*, the first end face 3*a* having the plugged portion 6, and the second end face 3*b* being opened; and a porous partition wall 5 that defines the first cells 4*a* and the second cells 4*b*. Each of the first cells 4*a* and each of the second cells 4*b* are alternately arranged adjacent to each other across the partition wall 5, whereby each of the first end face 3*a* and the second end face 3*b* presents a honeycomb shape.

When an exhaust gas containing PMs such as soot is fed to the first end face 3*a* on an upstream side of the pillar shaped honeycomb filter 1, the exhaust gas is introduced into the first cells 4*a* and proceeds in the first cells 4*a* toward the downstream. Since the first cells 4*a* have the plugged portions 6 on the second end face 3*b* on the downstream side, the exhaust gas passes through the porous partition wall 5 separating the first cells 4*a* from the second cells 4*b*, and flows into the second cells 4*b*. Since the PMs cannot pass through the partition wall 5, they are collected and deposited in the first cells 4*a*. After the PMs are removed, the clean exhaust gas that has flowed into the second cells 4*b* proceeds in the second cells 4*b* toward the downstream and flows out from the second end face 3*b* on the downstream side.

Non-limiting Examples of materials for forming the pillar shaped honeycomb filter 1 include porous ceramics. The ceramics include cordierite, mullite, zirconium phosphate, aluminum titanate, silicon carbide, silicon-silicon carbide composites (e.g., Si-bonded SiC), cordierite-silicon carbide composites, zirconia, spinel, indialite, sapphirine, corundum, titania, silicon nitride and the like. These ceramics may be used alone or in combination of two or more kinds.

The pillar shaped honeycomb filter 1 may support a catalyst for assisting PM combustion on a surface of the partition wall 5 or inside the partition wall 5. Examples of the catalyst include precious metals (Pt, Pd, Rh, and the like), alkali metals (Li, Na, K, Cs, and the like), alkaline earth metals (Ca, Ba, Sr, and like), rare earths (Ce, Sm, Gd, Nd, Y, Zr, Ca, La, Pr, and the like), and transition metals (Mn, Fe, Co, Ni, Cu, Zn, Sc, Ti, V, Cr, and the like).

Examples of shapes of the end faces of the pillar shaped honeycomb structure include, but not limited to, round shapes such as a circular shape, an oval shape, a race track shape and an elliptical shape, and polygonal shapes such as a triangular shape and a quadrangular shape. It should be noted that the illustrated pillar shaped honeycomb filter 1 is an example in the case where the shapes of the end faces are circular and the outer shape is pillar shaped.

Examples of shapes of the cells (the first cells 4*a* and the second cells 4*b*) in the cross section perpendicular to the flow path direction of the cells include, but not limited to, preferably a quadrangle, a hexagon, an octagon, or a combination thereof. Among them, a square and hexagon are preferred. Such a cell shape results in a decreased pressure loss when the fluid is allowed to flow through the pillar shaped honeycomb filter 1.

A cell density (the number of cells per unit cross-sectional area) is not particularly limited, and it may be, for example, from 6 to 2000 cells/square inch (from 0.9 to 311 cells/cm$^2$), and more preferably from 50 to 1000 cells/square inch (from 7.8 to 155 cells/cm$^2$), and even more preferably from 100 to 400 cells/square inch (from 15.5 to 62.0 cells/cm$^2$).

The pillar shaped honeycomb filter 1 can also be provided as an integrally formed product. The pillar shaped honeycomb filter 1 can also be provided as a segment joined body by joining and integrating outer side surfaces of a plurality of pillar shaped honeycomb segments each having the outer peripheral wall 2. By providing the pillar shaped honeycomb filter 1 as the segment joined body, thermal shock resistance can be increased.

The pillar shaped honeycomb filter 1 can be produced using a method known in the art. The method for producing the pillar shaped honeycomb filter 1 is described below as an example.

First, a raw material composition containing a ceramic raw material, a dispersion medium, a pore former and a binder is kneaded to form a green body. The green body is then extruded to form a desired pillar shaped honeycomb formed body. The raw material composition may optionally contain any additive such as a dispersant. In extrusion molding, a die having a desired overall shape, cell shape, partition wall thickness, cell density and the like can be used.

After the pillar shaped honeycomb formed body is dried, plugged portions are formed on both end faces of the pillar shaped honeycomb formed body, and the plugged portions are then dried to obtain a pillar shaped honeycomb formed body having the plugged portions. After that, the pillar shaped honeycomb formed body is subjected to degreasing and firing to produce a pillar shaped honeycomb filter 1.

The ceramic raw material that can be used herein includes a raw material capable of forming the above ceramics after firing. The ceramic raw material can be provided, for example, in the form of powder. Examples of the ceramic raw material include raw materials for obtaining ceramics such as cordierite, mullite, zircon, aluminum titanate, silicon carbide, silicon nitride, zirconia, spinel, indialite, sapphirine, corundum, and titania. Specific examples include, but not limited to, silica, talc, alumina, kaolin, serpentine, pyrophyllite, brucite, boehmite, mullite, magnesite, and aluminum hydroxide. The ceramic raw material may be used alone or in combination of two or more types.

For filter applications such as DPFs and GPFs, cordierite can be preferably used as the ceramic. In this case, a cordierite-forming raw material can be used as the ceramic raw material. The cordierite-forming raw material is a raw material that will form cordierite by firing. The cordierite-forming raw material is preferably composed of a chemical composition having 30 to 45% by mass of alumina ($Al_2O_3$) (including an amount of aluminum hydroxide converted to alumina), 11 to 17% by mass of magnesia (MgO), and 42 to 57% by mass of silica ($SiO_2$).

Examples of the dispersion medium include water or a mixed solvent of water and an organic solvent such as alcohol. The water can be more preferably used.

The pore former is not particularly limited as long as it forms pores after firing. Examples include wheat flour, starch, foaming resins, water-absorbing resins, porous silica, carbon (e.g., graphite), ceramic balloons, polyethylene, polystyrene, polypropylene, nylon, polyester, acrylics and phenols. The pore former may be used alone or in combination with two or more types. From the viewpoint of increasing the porosity of the fired body, the content of the pore former is preferably 0.5 parts by mass or more, and more preferably 2 parts by mass or more, and even more preferably 3 parts by mass or more, based on 100 parts by mass of the ceramic raw material. From the viewpoint of ensuring the strength of the fired body, the content of the pore former is preferably 10 parts by mass or less, and more preferably 7 parts by mass or less, and even more preferably 4 parts by mass or less, based on 100 parts by mass of the ceramic raw material.

Examples of the binder include organic binders such as methyl cellulose, hydroxypropyl methyl cellulose, hydroxyethyl cellulose, carboxymethyl cellulose, and polyvinyl alcohol. Among them, it is preferable to use methyl cellulose in combination with hydroxypropyl methyl cellulose. Further, the content of the binder is preferably 4 parts by mass or more, and more preferably 5 parts by mass or more, and 6 parts by mass, based on 100 parts by mass of the ceramic raw material, in terms of increasing the strength of the honeycomb formed body. The content of the binder is preferably 9 parts by mass or less, and more preferably 8 parts by mass or less, and even more preferably 7 parts by mass or less, based on 100 parts by mass of the ceramic raw material, in terms of suppressing cracking due to abnormal heat generation in the firing step. The binder may be used alone or in combination with two or more types.

The dispersant that can be used includes ethylene glycol, dextrin, fatty acid soaps, polyether polyol and the like. The dispersant may be used alone or in combination with two or more types. The content of the dispersant is preferably from 0 to 2 parts by mass based on 100 parts by mass of the ceramic raw material.

The method for plugging the end faces of the pillar shaped honeycomb formed body is not particularly limited, and a well-known method can be employed. Materials of the plugged portions 6 are not particularly limited. Ceramics are preferable in terms of strength and heat resistance. The ceramics are preferably a ceramic material containing at least one selected from the group consisting of cordierite, mullite, zircon, aluminum titanate, silicon carbide, silicon nitride, zirconia, spinel, indialite, sapphirine, corundum, and titania. Even more preferably, the plugged portions 6 have the same material composition as that of a main body portion of the honeycomb formed body, because it can provide the same expansion coefficient during firing, leading to improved durability.

After drying the honeycomb formed body, degreasing and firing can be carried out to produce the pillar shaped honeycomb filter. For conditions of the drying step, the degreasing step, and the firing step, known conditions may be used according to the material composition of the honeycomb formed body, and no specific explanation is required. However, specific examples of the conditions are given below.

In the drying step, conventionally known drying methods such as hot air drying, microwave drying, dielectric drying, drying under reduced pressure, vacuum drying, and freeze drying can be used. Among them, a drying method that combines the hot air drying and microwave drying or dielectric drying is preferable in that the entire formed product can be quickly and uniformly dried. When forming the plugged portions, it is preferable to form the plugged portions on both end faces of the dried honeycomb formed body and then dry the plugged portions.

Next, the degreasing step will be described. A combustion temperature of the binder is about 200° C., and a combustion temperature of the pore former is about from 300 to 1000° C. Therefore, the degreasing step may be carried out by heating the honeycomb formed boy at a temperature in a range of from about 200 to 1000° C. A heating time is not particularly limited. It is generally about from 10 to 100 hours. The honeycomb formed body after the degreasing step is referred to as a calcined body.

Depends on the material composition of the honeycomb formed body, the firing step can be carried out, for example, by heating the calcined body to 1350 to 1600° C. and holding it for 3 to 10 hours.

The fired honeycomb formed body may be used as it is as a filter, or porous films for collecting PMs may be separately formed on the partition wall 5 in order to improve the PN collection efficiency. Any known method can be employed as the method for forming the porous films. In an embodiment, the porous film can contain, in total, 50% by mass or more of one or more selected from silicon carbide, cordierite, alumina, silica, mullite and aluminum titanate.

<Housing Portion 10>

The housing portion 10 is a member that can house the pillar shaped honeycomb filter 1.

The shape of the housing portion 10 is not particularly limited, but it may be appropriately set according to the shape of the pillar shaped honeycomb filter 1. For example, when the outer shape of the pillar shaped honeycomb filter 1 is cylindrical, the housing portion 10 can be cylindrical.

In the housing portion 10, the pillar shaped honeycomb filter 1 is housed so that the first end face 3a faces the introduction pipe 20 side and the second end surface 3b faces the discharge pipe 30 side.

Examples of the material used for the housing portion 10 include metals, ceramics, and the like. Examples of the metals include stainless steel, titanium alloys, copper alloys, aluminum alloys, brass and the like. The material of the housing portion 10 is preferably stainless steel because of its high durability and reliability.

<Introduction Pipe 20 and Discharge Pipe 30>

The introduction pipe 20 and the discharge pipe 30 are members through which a gas can flow, and which are connected to the housing portion 10. The introduction pipe 20 is located on the upstream side of the housing portion 10 in the gas flow direction X. Further, the discharge pipe 30 is located on the downstream side of the housing portion 10 in the gas flow direction X.

The shapes of the introduction pipe 20 and the discharge pipe 30 are not particularly limited. Each of them may have a cylindrical shape in which a cross section perpendicular to the gas flow direction X is circular; a rectangular cylindrical shape in which the cross section is triangular, quadrangular, pentagonal, or a hexagonal; and an elliptical cylindrical shape in which the cross section is elliptical. Among them, the introduction pipe 20 and the discharge pipe 30 are preferably cylindrical.

Each of the introduction pipe 20 and the discharge pipe 30 has any diameter (outer diameter and inner diameter), and a part of them may have an increased or decreased diameter. Such a structure can lead to easy connection to other members or easy arrangement of other members, for example.

Examples of the materials used for the introduction pipe 20 and the discharge pipe 30 include metals, ceramics, and the like. Examples of the metals include stainless steel, titanium alloys, copper alloys, aluminum alloys, brass and the like. The materials of the introduction pipe 20 and the discharge pipe 30 are preferably stainless steel because of its high durability and reliability.

<Particle Generation Portion 40>

The particle generation portion 40 is a portion that generates particles to be introduced into the pillar shaped honeycomb filter 1. The particle generation portion 40 can generate a gas containing particles. Example of the gas in the gas containing particles include, but not particularly limited to, air, nitrogen, helium, hydrogen, argon, and the like. Among them, the air is particularly preferable from the viewpoint of cost and safety.

The particles generated by the particle generating portion 40 include, but not limited to, soot particles, carbon particles, oil particles such as DEHS (bis (2-ethylhexyl) sebacate) particles, NaCl particles, and resin particles such as polystyrene latex particles. A device capable of generating those particles is commercially available. Therefore, the commercially available device can be used as the particle generation portion 40.

The particle generating portion 40 is not particularly limited, and for example, a soot particle generator capable of generating soot particles can be used. The soot particle generator is connected to, for example, a propane source, a nitrogen source and an air source, and can generate soot particles by incomplete combustion of propane.

The inspection accuracy can be improved by a particle size distribution of the particles generated by the particle generation portion 40, which is closer to the particle size distribution of the PMs contained in the actual exhaust gas. For example, a median diameter D50 (hereinafter, the median diameter 50 is referred to as an "average particle diameter") based on the number of PMs contained in the automobile exhaust gas is from 50 to 100 nm in a cumulative particle size distribution obtained by an electrostatic particle classifier and an agglomerated particle counter, and the like. Therefore, it is ideal that the average particle diameter of the particles generated by the particle generation portion 40 is also in that range. However, even if the particles have a particle size distribution different from that of the PMs contained in the actual exhaust gas, those particles can also be used because the collection mechanism is identical up to about 1000 nm.

The collection of the particles is mainly classified into the following four types:

(I) diffusion (collected by movement different from the flow due to the Brownian motion of particles);
(II) interruption (corrected by physical contact even if particles are carried by the flow);
(III) sedimentation (large particles deviate from the flow due to gravity and cannot pass through); and
(IV) inertia (large particles are collected without being carried in the flow even if the flow direction changes).

For particles having a particle diameter up to about 1000 nm, the diffusion and interruption are dominant, so that the use of particles having a lower particle diameter can allow the actual collection performance to be simulated.

Therefore, the average particle diameter of the particles generated by the particle generating portion 40 is preferably from 100 to 1000 nm. By controlling the average particle diameter of the particles to such a range, the inspection accuracy of the collection performance can be stably improved.

Further, in the case of the inspection of the collection performance of the pillar shaped honeycomb filter 1 having a general collection ability, the average particle diameter of the particles may be in the above range. However, in the case of the inspecting of the collection performance of the pillar shaped honeycomb filter 1 having a higher collection ability, an average particle diameter of 300 nm or more results in substantially the same inspection result, so that it is difficult to obtain details of the collection performance. Therefore, in such a case, the average particle diameter of the particles is preferably 30 nm or more and less than 300 nm, and more preferably from 100 to 250 nm. By controlling the average particle diameter of the particles to such a range, the details of the collecting performance can be obtained even if the pillar shaped honeycomb filter 1 having a higher collecting ability is inspected, so that the inspection accuracy of the collecting performance can be improved.

<Particle Introduction Portion 50>

The particle introduction portion 50 is a portion that introduces the particles generated by the particle generation portion 40 into the introduction pipe 20. The particle introduction portion 50 and the particle generation portion 40 can be connected by using a tubular member such as a tube.

The particle introduction portion 50 is not particularly limited, but it is preferable to use a sprayer from the viewpoint of uniformly introducing the particles into the introduction pipe 20.

Figure 4:
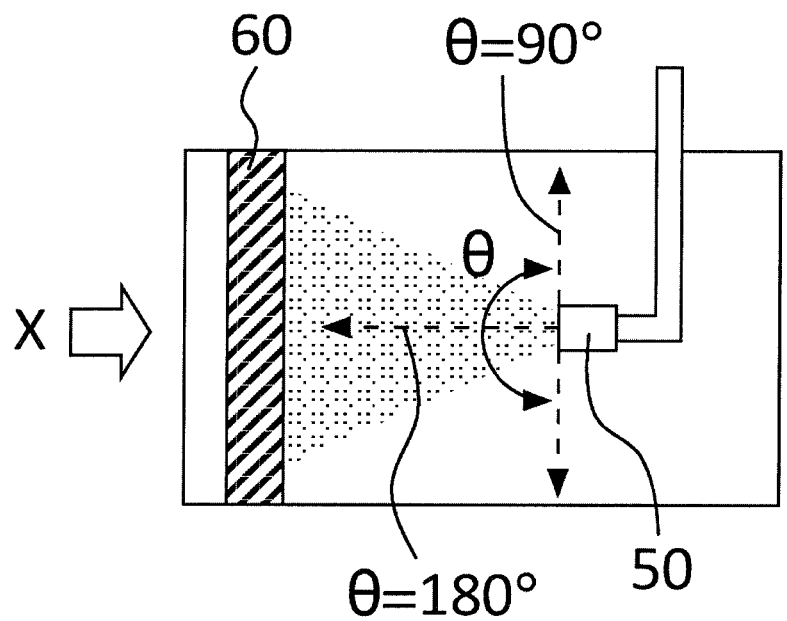
FIG. 4 is an enlarged view of the periphery of the particle introduction portion in FIG. 1.

As shown in FIG. 4, a direction of the particles introduced into the particle introduction portion 50 preferably has an angle θ of more than 90°, and more preferably an angle θ of from 100 to 180°, and still more preferably an angle θ of from 150 to 180°, and particularly preferably an angle θ of 180°, relative to the gas flow direction X. It should be noted that FIG. 4 is an enlarged view of the periphery of the particle introduction portion 50 shown in FIG. 1. By thus controlling the introduction direction of the particles, the particles are more easily diffused into the gas, so that an effect of suppressing the deviation of the concentration distribution of the particles in the plane perpendicular to the gas flow direction X can be enhanced. The number of the particles is measured by the particle counters 70a, 70b using the particles in which the deviation of the concentration distribution has been suppressed, so that the inspection accuracy of the collection performance can be further improved.

The particle introduction portion 50 preferably has a particle discharge port at a position facing the gas flow direction X, and more preferably it has a particle discharge port at a position opposing to the gas flow direction X. By providing the discharge port at such a position, the particles can be introduced so as to have an angle θ of more than 90° relative to the gas flow direction X.

Various conditions such as an amount and a rate of particles introduced in the particle introduction portion 50 may be appropriately set depending on the type of the particle introduction portion 50, the size of the introduction pipe 20, and the like, and are not particularly limited.

<Gas Stirring Portion 60>

A gas stirring portion 60 is a member having a function of stirring a gas. The gas stirring portion 60 is arranged in the introduction pipe 20 on the upstream side of the particle introduction portion 50 in the gas flow direction X.

The gas stirring portion 60 is not particularly limited, but it may preferably be a gas stirring plate.

Figure 5:
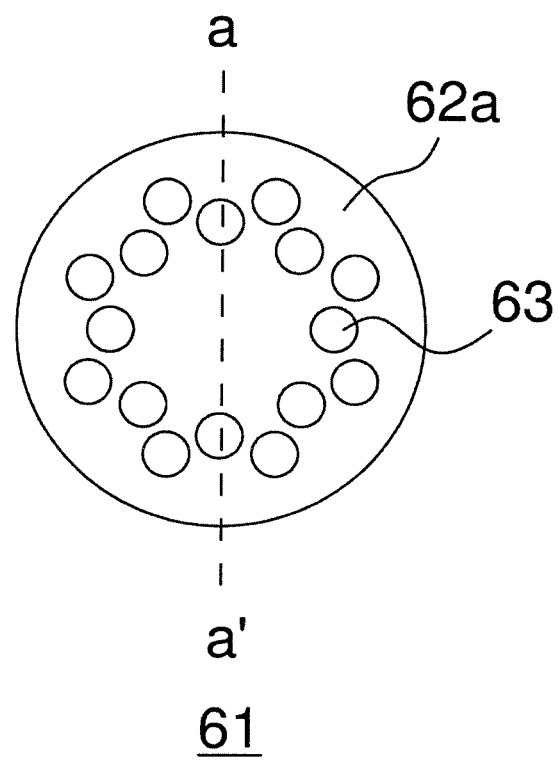
FIG. 5 is a plane view of a gas stirring plate used in an inspection device for a pillar shaped honeycomb filter according to an embodiment of the present invention.

Here, a plane view of a typical gas stirring plate (a plane view seen from the upstream side of the gas flow direction X) is shown in FIG. 5. Further, a cross-sectional view taken along the line a-a' in FIG. 5 is shown in FIG. 6.

Figure 6:
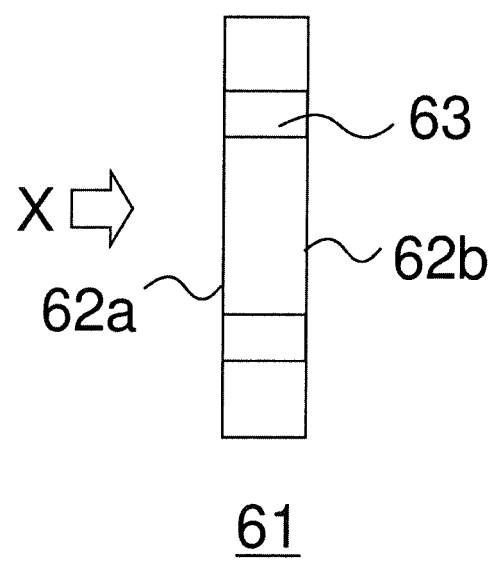
FIG. 6 is a cross-sectional view taken along the line a-a' of the gas stirring plate in FIG. 5.

As shown in FIGS. 5 and 6, the gas stirring plate 61 has a pair of planes 62a, 62b perpendicular to the gas flow direction X, and a plurality of openings 63 penetrating the pair of planes 62a, 62b.

The use of the gas stirring plate 61 as the gas stirring portion 60 leads to a negative pressure on a slip stream side (plane 62b side) of the gas stirring plate 61, resulting in a backflow of the gas to form a recirculation flow. By introducing the particles from the particle introduction portion 50 into that portion, the particles are diffused into the gas while being involved in the recirculation flow, so that the deviation of the concentration distribution of the particles in the plane perpendicular to the gas flow direction X is suppressed. As a result, the particles can be uniformly fed to the pillar shaped honeycomb filter 1 to be inspected. Further, the gas stirring plate 61 has a simpler structure than that of a stirring device having a rotary blade mechanism and does not require any external electric power, so that various costs can be suppressed.

In the gas stirring plate 61, the plurality of openings 63 are preferably provided in a region on an outer peripheral side of the gas stirring plate 61. By providing the plurality of openings 63 in such a region, a recirculation flow is easily formed on the slip stream side of the gas stirring plate 61, so that the effect of diffusing the particles into the gas is enhanced.

Here, the region on the outer peripheral side of the gas stirring plate 61 refers to a region from the outer peripheral portion of the gas stirring plate 61 to ½ of a diameter (a radius, for example in the case of a disk shape) from the center of the gas stirring plate 61 to the outer circumference.

In the gas stirring plate 61, the plurality of openings 63 preferably have an opening ratio of from 5 to 50%, and more preferably from 10 to 40%. By controlling the opening ratio to such a range, the recirculation flow is easily formed on the slip stream side of the gas stirring plate 61, so that the effect of diffusing the particles into the gas is enhanced.

Here, the opening ratio means, for example, a ratio of an area of the openings 63 to the total area of the plane **62*a* and the openings 63 in the plane view of FIG. 5**.

The recirculation flow on the slip stream side of the gas stirring plate 61 is more likely to be formed as a flow velocity of the gas flowing through the introduction pipe 20 is higher (a flow rate is higher). Therefore, the flow rate of the gas is preferably from 500 to 10000 L/min.

The size of the gas stirring plate 61 is not particularly limited, and it may be appropriately adjusted depending on the size of the introduction pipe 20 in which the gas stirring plate 61 is arranged. For example, the outer diameter of the gas stirring plate 61 can correspond to the inner diameter of the introduction pipe 20.

Examples of the material used for the gas stirring plate 61 include metals, ceramics, and the like. Examples of the metals include stainless steel, titanium alloys, copper alloys, aluminum alloys, brass and the like. The material of the gas stirring plate 61 is preferably stainless steel because of its high durability and reliability.

A distance between the particle introduction portion 50 and the gas stirring portion 60 in the gas flow direction X is preferably 3 times or less, more preferably 2.5 times or less, the inner diameter of the introduction pipe 20 at the position where the gas stirring portion 60 is arranged. By controlling the distance between the particle introduction portion 50 and the gas stirring portion 60 to such a range, the particles can be stably introduced into the region where the recirculation flow is formed, so that the effect of diffusing the particles into the gas can be enhanced.

The gas (gas serving as a carrier for the particles) stirred by the gas stirring portion 60 includes, but not limited to, air, nitrogen, helium, hydrogen, and argon. Among them, the air is preferable from the viewpoint of cost and safety.

<Particle Counters 70a, 70b>

The particle counters 70a, 70b are devices for measuring the number of particles in the gas flowing through the introduction pipe 20 and the discharge pipe 30. The particle counter 70a is arranged in the introduction pipe 20 on the downstream side of the particle introduction portion 50 in the gas flow direction X. Further, the particle counter 70b is arranged in the discharge pipe 30.

The particle counters 70a, 70b are not particularly limited as long as they can measure the number of particles contained in the gas. However, when inspecting the collection performance of the pillar shaped honeycomb filter 1 having a higher collection capacity, it is preferable to use particles having a smaller average particle diameter as described above. In order to measure such particles having a smaller average particle diameter, it is preferable to select particle counters 70a, 70b that can measure the number of particles having a particle diameter of 100 nm or more.

Examples of the particle counters 70a, 70b that can be used herein include an optical particle counter, a laser photometer, and a dust collector. Among them, the optical particle counter is preferably used. The use of the optical particle counter enables the number of particles to be easily and accurately measured. Since the optical particle counter is commercially available (e.g., KC-24 or KC-22B from RION Co., Ltd.), the commercially available product can be used as the particle counters 70a, 70b.

A distance between the particle introduction portion 50 and the particle counter 70a arranged in the introduction pipe 20 in the gas flow direction X may preferably be at least twice the inner diameter of the introduction pipe 20 at the position where the particle counter 70a is arranged. By arranging the particle counter 70a in such a range, the number of particles contained in the gas can be accurately measured.

Figure 7:
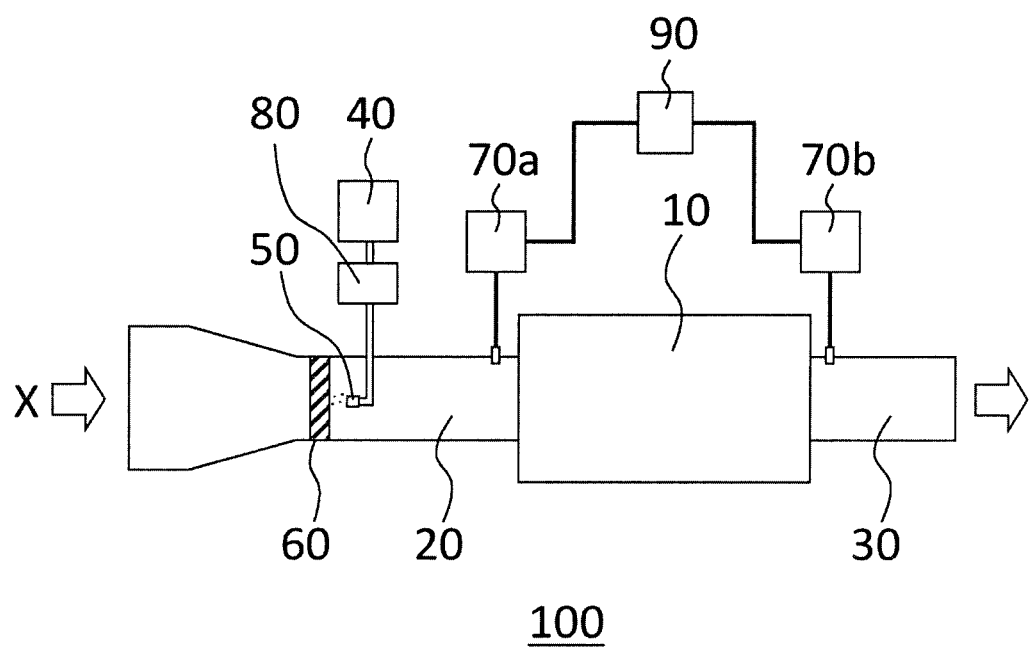
FIG. 7 is a schematic view of another inspection device for a pillar shaped honeycomb filter according to an embodiment of the present invention.

The inspection device 100 for the pillar shaped honeycomb filter 1 according to an embodiment of the present invention may optionally further include a diluter 80 for adjusting the concentration of particles, provided between the particle generation portion 40 and the particle introduction portion 50, as shown in FIG. 7. Since the diluter 80 having such a function is commercially available (e.g., Model 3332 from TSI), the commercially available product can be used.

When the optical particle counters are selected as the particle counters 70a, 70b, it is desirable to reduce the concentration of the particles in the gas because the optical particle counter is easily contaminated by the particles. Therefore, the diluter 80 can be provided between the particle generation portion 40 and the particle introduction portion 50, so that the concentration of particles can be adjusted, thereby suppressing contamination of the optical particle counter.

The diluter 80 preferably dilutes the concentration of the particles generated by the particle generation portion 40 by 2 to 1000 times. With such a dilution ratio, the contamination of the optical particle counter can be stably suppressed.

The inspection device 100 for the pillar shaped honeycomb filter 1 according to the embodiment of the present invention may optionally further include a calculation unit 90 for calculating a collection efficiency of particles based on the number of the particles measured by the particle counters 70a, 70b arranged in the introduction pipe 20 and the discharge pipe 30 as shown in FIG. 7. Examples of the calculation unit 90 having such a function include a computer and the like.

By providing such a calculation unit 90, the collection efficiency can be calculated in real time, so that the inspection can be rapidly performed.

(2) Inspection Method for Pillar Shaped Honeycomb Filter 1

An inspection method for the pillar shaped honeycomb filter 1 according to an embodiment of the present invention includes: a particle generation step (S1); a particle introduction step (S2); a particle feed step (S3); and a particle measurement step (S4). By performing these steps, the inspection accuracy of the collection performance of the pillar shaped honeycomb filter 1 can be improved. This inspection method can be performed using the inspection device 100 for the pillar shaped honeycomb filter 1 as described above.

The particle generation step (S1) is a step of generating particles. This step can be carried out by activating the particle generation portion 40 in the inspection device 100 for the pillar shaped honeycomb filter 1.

The particle introduction step (S2) is a step of introducing the particles generated in the particle generation step (S1) into the gas stirred by the gas stirring portion 60. This step can be carried out by using the particle introduction portion 50 in the inspection device 100 for the pillar shaped honeycomb filter 1 to introduce the particles generated by the particle generation portion 40 into the introduction pipe 20. By introducing the particles into the gas by such a method, the particles are easily diffused into the gas, so that the deviation of the concentration distribution of the particles can be suppressed.

A direction of the particles introduced in the particle introduction step (S2) preferably has an angle θ of more than 90° relative to the gas flow direction X. By controlling the introduction direction of the particles in such a method, the particles are more easily diffused into the gas, so that the effect of suppressing the deviation of the concentration distribution of the particles in the plane perpendicular to the gas flow direction X can be enhanced.

The particle feed step (S3) is a step of feeding the gas having the introduced particles to the pillar shaped honeycomb filter 1. Since the particles in the gas fed to the pillar shaped honeycomb filter 1 have the suppressed deviation of the concentration distribution, the amount of particles fed in the pillar shaped honeycomb filter 1 can be made uniform. As a result, even if the direction of the pillar shaped honeycomb filter 1 and the arrangement method are different, it will be difficult for measured values to vary, so that the inspection accuracy of the collection performance is improved.

The particle measurement step (S4) is a step of measuring the number of particles in the gas on the upstream side and on the downstream side of the pillar shaped honeycomb filter 1 in the gas flow direction X. This step is carried out using the particle counters 70a, 70b in the inspection device 100 for the pillar shaped honeycomb filter 1.

The inspection method for the pillar shaped honeycomb filter 1 according to the embodiment of the present invention may optionally further include a particle concentration diluting step (S5) for diluting the concentration of the particles generated in the particle generation step (S1). This step can be carried out between the particle generation step (S1) and the particle introduction step (S2), and is carried out using the diluter 80 in the inspection device 100 for the pillar shaped honeycomb filter 1.

In the particle concentration diluting step (S5), the concentration of the particles generated in the particle generation step is preferably diluted by 2 to 1000 times as described above. This step can allow the concentration of the particles to be adjusted, so that any contamination of the optical particle counters is suppressed.

The inspection method for the pillar shaped honeycomb filter 1 according to the embodiment of the present invention may optionally further include a collection efficiency calculation step (S6) for calculating the particle collection efficiency from the number of particles obtained in the particle measurement step (S4). The collection efficiency can be calculated by the following equation:

Collection efficiency [%]=(number of particles in gas on upstream side of pillar shaped honeycomb filter 1−number of particles in gas on downstream side of pillar shaped honeycomb filter 1)/number of particles in gas on upstream side of pillar shaped honeycomb filter 1×100.

The collection efficiency calculation step (S6) can be carried out after the particle measurement step (S4), and is carried out using the calculation unit 90 in the inspection device 100 for the pillar shaped honeycomb filter 1. This step can allow the collection efficiency to be calculated in real time, enabling rapid inspection.

DESCRIPTION OF REFERENCE NUMERALS 1 pillar shaped honeycomb filter
2 outer peripheral wall
3a first end face
3b second end face
4a first cell
4b second cell
5 partition wall
6 plugged portion
10 housing portion
20 introduction pipe
30 discharge pipe
40 particle generation portion
50 particle introduction portion
60 gas stirring portion
61 gas stirring plate
62a, 62b plane
63 opening
70a, 70b particle counter
80 diluter
90 calculation unit
100 inspection device
X gas flow direction

The invention claimed is:

1. An inspection device for a pillar shaped honeycomb filter, wherein the inspection device comprises:
a housing portion that can house a pillar shaped honeycomb filter;
an introduction pipe and a discharge pipe through which a gas can flow, each of the introduction pipe and the discharge pipe being connected to the housing portion;
a particle generation portion for generating particles;
a particle introduction portion for introducing the particles generated by the particle generation portion into the introduction pipe;
a gas stirring portion arranged in the introduction pipe on an upstream side of the particle introduction portion in a gas flow direction; and
particle counters for measuring the number of particles, the particle counters being arranged in the introduction pipe and the discharge pipe on a downstream side of the particle introduction portion in the gas flow direction,
wherein the gas stirring portion is a gas stirring plate having a pair of planes perpendicular to the gas flow direction and having a plurality of openings penetrating the pair of planes, and the plurality of openings are provided in a region on an outer peripheral side of the gas stirring plate.

2. The inspection device for a pillar shaped honeycomb filter according to claim 1, wherein the plurality of openings have an opening ratio of from 5 to 50%.

3. The inspection device for a pillar shaped honeycomb filter according to claim 1, wherein a direction of the particles introduced in the particle introduction portion has an angle of more than 90° relative to the gas flow direction.

4. The inspection device for a pillar shaped honeycomb filter according to claim 1, wherein the particles have an average particle diameter of from 100 to 1000 nm.

5. The inspection device for a pillar shaped honeycomb filter according to claim 1, wherein a flow rate of the gas is from 500 to 10000 L/min.

6. The inspection device for a pillar shaped honeycomb filter according to claim 1, wherein the particle counters can measure the number of the particles having a particle diameter of 100 nm or more.

7. The inspection device for a pillar shaped honeycomb filter according to claim 1, wherein each of the particle counters is an optical particle counter.

8. The inspection device for a pillar shaped honeycomb filter according to claim 1, further comprising a diluter for adjusting the concentration of the particles, provided between the particle generation portion and the particle introduction portion.

9. The inspection device for a pillar shaped honeycomb filter according to claim 8, wherein the diluter dilutes the concentration of the particles generated in the particle generation portion by 2 to 1000 times.

10. The inspection device for a pillar shaped honeycomb filter according to claim 1, further comprising a calculation unit for calculating a collection efficiency of the particles based on the number of the particles measured by the particle counters arranged in the introduction pipe and the discharge pipe.

11. The inspection device for a pillar shaped honeycomb filter according to claim 1, wherein a distance between the particle introduction portion and the gas stirring portion in the gas flow direction is 3 times or less an inner diameter of the introduction pipe at the position where the gas stirring portion is arranged.

12. The inspection device for a pillar shaped honeycomb filter according to claim 1, wherein a distance between the particle introduction portion and the particle counter arranged in the introduction pipe in the gas flow direction is at least twice an inner diameter of the introduction pipe at the position where the particle counter is arranged.

13. An inspecting method for a pillar shaped honeycomb filter, wherein the method comprises:
a particle generation step of generating particles;
a particle introduction step of introducing the particles generated in the particle generation step into a gas stirred by a gas stirring portion;
a particle feed step of feeding the gas having the introduced particles to the pillar shaped honeycomb filter; and
a particle measurement step of measuring the number of particles in the gas on an upstream side and a downstream side of the pillar shaped honeycomb filter in a flow direction of the gas, wherein the gas stirring portion is a gas stirring plate having a pair of planes perpendicular to the gas flow direction and having a plurality of openings penetrating the pair of planes, and wherein the plurality of openings are provided in a region on an outer peripheral side of the gas stirring plate.

14. The inspection method for a pillar shaped honeycomb filter according to claim 13, wherein the plurality of openings have an opening ratio of from 5 to 50%.

15. The inspection method for a pillar shaped honeycomb filter according to claim 13, wherein a direction of the particles introduced in the particle introduction step has an angle of more than 90° relative to the gas flow direction.

16. The inspection method for a pillar shaped honeycomb filter according to claim 13, wherein the particles have an average particle diameter of from 100 to 1000 nm.

17. The inspection method for a pillar shaped honeycomb filter according to claim 13, wherein a flow rate of the gas is from 500 to 10000 L/min.

18. The inspection method for a pillar shaped honeycomb filter according to claim 13, wherein the particle measurement step comprises measuring the number of the particles having a particle diameter of 100 nm or more.

19. The inspection method for a pillar shaped honeycomb filter according to claim 13, wherein the number of the particles is measured using optical particle counters.

20. The inspection method for a pillar shaped honeycomb filter according to claim 13, further comprising a particle concentration diluting step of diluting the concentration of the particles generated in the particle generation step.

21. The inspection method for a pillar shaped honeycomb filter according to claim 20, wherein the particle concentration diluting step comprises diluting the concentration of the particles generated in the particle generation step by 2 to 1000 times.

22. The inspection method for a pillar shaped honeycomb filter according to claim 13, further comprising a collection efficiency calculation step of calculating a collection efficiency of the particles from the number of the particles obtained in the particle measurement step.

* * * * *